United States Patent [19]

Hamer et al.

[11] Patent Number: 4,599,308
[45] Date of Patent: Jul. 8, 1986

[54] PROTEIN FROM SV40 RECOMBINANTS

[76] Inventors: Dean H. Hamer, 1828 Calvert St., N.W., Washington, D.C. 20005; Marian Kaehler, R.R. 3, Decorah, Iowa 52101; Philip Leder, 5106 Benton Ave., Bethesda, Md. 20014

[21] Appl. No.: 536,579

[22] Filed: Sep. 29, 1983

Related U.S. Application Data

[63] Continuation of Ser. No. 309,110, Oct. 6, 1981, abandoned.

[51] Int. Cl.[4] .................... C12P 21/00; C12N 15/00
[52] U.S. Cl. .................................. 435/68; 435/172.3; 935/32; 935/34; 935/60
[58] Field of Search .................. 435/68, 70, 71, 172.3; 935/32, 34, 60

[56] References Cited

PUBLICATIONS

Hamer et al, Cell vol. 21 pp. 697–708 Oct. 1980.
Hamer et al, Nature vol. 281 pp. 35–40 (1979).
Goeddel et al, Nature vol. 281 pp. 544–548 (1979).
Sambrook et al, Genetic Engineering vol. 2 Plenum Press pp. 103–114 (1980).
Mulligan et al, Science vol. 209 pp. 1422–1427 (Sep. 1980).
Mulligan et al, Nature vol. 277 pp. 108–114 (1979).
Goff et al, J. Mol. Biol. vol. 133 pp. 359–383 (1979).

*Primary Examiner*—Alvin E. Tanenholtz
*Attorney, Agent, or Firm*—John S. Roberts, Jr.

[57] ABSTRACT

An *E. Coli* plasmid SV40 vector recombinant is cloned to a gene of interest and amplified in bacteria. The SV40 vector-gene of interest can be introduced into eukaryotic cells by transformation or transfection and the gene of interest produces its protein product.

2 Claims, 1 Drawing Figure

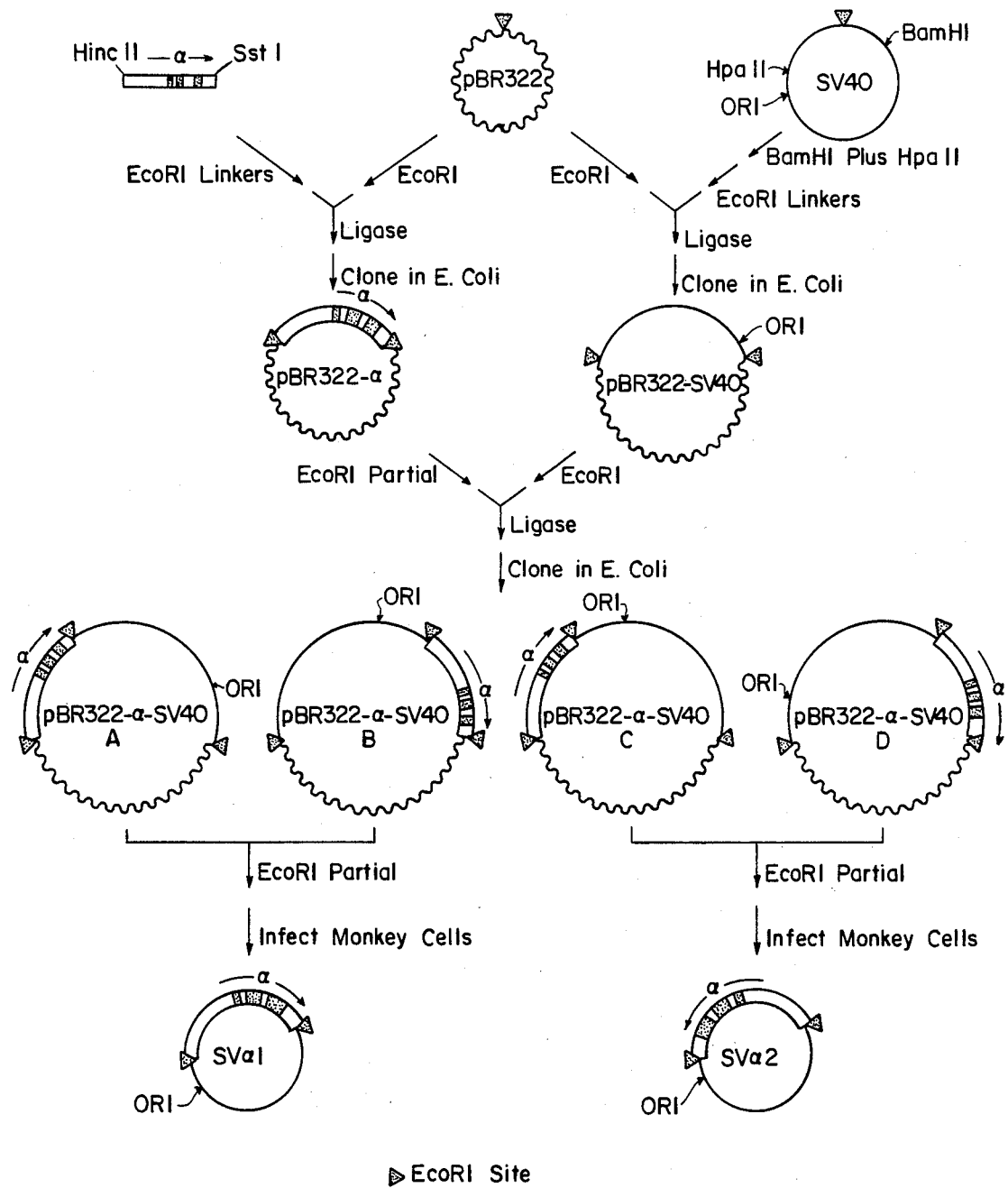

PROTEIN FROM SV40 RECOMBINANTS

This application is a continuation, of application Ser. No. 309,110, filed Oct. 6, 1981 and now abandoned.

PRIOR ART STATEMENT

"DNA Cloning in Mammalian Cells with SV40 Vectors," *Genetic Engineering*, Vol. 2 (1980), edited by Setlow and Hollaender, Plenum Publishing Co., New York.

Hamer and Leder, *Cell*, Vol. 18, 1299-1302, December 1979.

Hamer, Kaehler & Leder, *Cell*, 21, 697-708, October 1980. This most recent publication is not prior art but included for pertinency to the invention.

BACKGROUND OF THE INVENTION

Simian virus (SV40) is one of the best characterized viruses and its DNA genome has been widely studied. The first attempts to apply recombinant DNA technology to introduce DNA segments ito animal cells have utilized SV40 as the vector. SV40 is also ideal as a vector because of its ability to transform cells from a wide variety of species. This means the SV40 recombinants can introduce foreign genetic information into cultued cells, or even animals, in a stable fashion.

Earlier work has formed the recombinants by *in vitro* manipulations. The present invention forms the recombinants by cloning in E. coli. This is decidedly quicker and cheaper. This is because bacterial clones (e.g., for colony hybridization) can be grown up in a few hours on inexpensive agar plates. In contrast, an SV40 plaque assay on monkey cells can take as long as two weeks and requires expensive tissue culture media, serum, a carbon dioxide incubator, etc.

SUMMARY OF THE INVENTION

SV40 DNA vectors can be cloned to a gene of interest to produce recombinant DNA. The cloning is done in E. coli, which technique is more rapid and easier than prior art techniques.

Examples of unique representative SV40 vectors are given and the ability to produce different proteins in eukaryotic cells by transformation or transfection demonstrated.

The FIGURE illustrates the recombinant formed according to the detailed description in Example 2.

DETAILS OF THE INVENTION

The SV40 genome. The genome of SV40 is a 5200 base-pair, covalently closed DNA circle. For convenience, the genome is divided into map units with the 0.00/1.00 point at the unique EcoRI restriction endonuclease site (The FIGURE). The structural and functional organization of the viral genome have been described in detail in two recent reviews [Kelly et al, (1977) in Advances in Virus Research (Lauffer et al eds.), Vol. 21, p. 86-173, Academic Press, New York; and Fareed et al (1977) in Ann. Rev. Biochem. (Snell et al, eds.) Vol. 46, pp. 471-522, Palo Alto, CA]. The complete nucleotide sequence of the viral DNA has been independently determined by two groups [Fiers, et al (1978) Nature, 273, 113-120; and Reddy et al (1978), Science 200, 494-502].

SV40 can undergo two types of interactions with cultured mammalian cells. In African green monkey kidney cells, which are the permissive host, the virus undergoes a productive cycle. The virus first attaches to the cell, penetrates it and uncoats. Shortly thereafter, the viral early gene region, which extends counterclockwise from 0.67 to 0.17 map units, is transcribed. This region, constituting the A complementation group, encodes the large form (T-antigen) and small form (t-antigen) of the viral tumor antigen. T-antigen is involved in both the initiation of viral DNA synthesis and in transformation and is required for both productive and nonproductive infection. The role of t-antigen is less certain, but it is not required for productive infection in tissue culture. The next step in the viral life cycle is the bidirectional replication of the viral DNA from the unique origin at 0.67 map units. Finally, the viral late gene region, extending clockwise from 0.67 to 0.17 map units, is expressed. These sequences code for the major viral coat protein VP1 (B/C complementation group) and the minor structural proteins VP2 and VP3 (D complementation group). At about three days post-infection, the cells are killed and a burst of infectious virus is released. SV40 does not shut off the synthesis of host cell macromolecules during the productive cycle. Even late in infection, normal or increased amounts of cellular DNA, RNA and proteins are produced.

In other types of cells, termed nonpermissive or semipermissive, this cycle is aborted prior to the onset of viral DNA replication. Instead, part or all of the viral genome becomes stably associated with the host cell, usually through integration into the chromosomal DNA. Such cells are said to be transformed and can be recognized by a variety of parameters related to loss of normal growth characteristics, e.g., ability to form colonies in agar or to cause tumors in animals. Transformed cells invariably express viral early functions but generally do not synthesize late gene products. SV40 transformation has been observed in several mammalian species including rat, mouse, hamster, and human.

SV40 Vectors. The vector is a DNA from SV40 or a derivative of SV40 cleaved by shear forces, nucleases or one or more restrictive enzymes and is a fragment which contains the origin of SV40 replication. The DNA may also contain a complete SV40 gene product or a functional early gene. The DNA from SV40 is cloned into a plasmid such as pBR322 or pSF2124. Vectors designated OY, 28C, BamV, Y182 and Y26 have been deposited with the ATCC and have received the following numbers respectively, ATCC 31968, ATCC 31965, ATCC 31966, ATCC 31964, and ATCC 31967.

The vectors are generated as follows:

OY. Wild type SV40 DNA is cleaved with BamHI at 0.14 map units and HpaII at 0.72 map units. The SV40 fragment extending clockwise from the Bam site to the HpaII site is ligated to EcoRI linkers in order to convert both sites to EcoRI sites. This is cloned into the E. coli plasmid pBR322 at its single EcoRI site.

28C. This is identical to OY except that it is constructed from the SV40 deletion mutant dl 2005 rather than from the wild type SV40 DNA. This allows one to clone approximately 300 more base pairs of DNA into the late region.

BamV. SV40 DNA is cleaved with BamHI at 0.14 map units and with HpaII at 0.72 map units. The HpaII site is converted by the use of a linker to a BamHI site. The fragment extending clockwise from the Bam site to the Hpa II site is cloned into plasmid pBR322 at a single BamHI site.

Y182. SV40 DNA is cleaved with BamHI at 0.14 map units and EcoRI at 0.00 map units. The fragment extending clockwise from the Bam site to the EcoRI site is cloned into plasmid pBR322 between a single Bam site and a single EcoRI site.

Y26. SV40 DNA is cleaved at its single EcoRI site and the entire genome is inserted into plasmid pSF2124 which has been cleaved at its single EcoRI site.

Map units and orientation are based on the standard SV40 map where the EcoRI site is designated as map position 0. The direction clockwise is the same direction as late transcription. The following examples are given for producing the recombinant.

EXAMPLE 1—Production of Y182-mouse $\beta^{maj}$ globin gene recombinant

The recombinant viruses were constructed as follows. A fragment of wild-type SV40 DNA extending from the BamHI site (map position 0.14) clockwise to the EcoRI site (map position 0.00) was cloned in the bacterial plasmid pBR322 between its single EcoRI and BamHI sites. The resulting pBR322-SV40 plasmid was opened at its single BamHI site and used as a vector for the 1500 bp chromosomal mouse $\beta^{maj}$ globin gene fragment extending from the BamHI site located 18 bp upstream from the second intervening sequence to the Xba I site 600 bp downstream from the polyadenylation site. (The globin gene Xba I site was converted to a BamHI site by ligation to a synthetic linker molecule as described by Hamer and Leder, 1979.) This procedure generated two types of pBR322-SV40-globin plasmids, one having the globin and viral late region coding sequences on the same strand and the other having these sequences on opposite strands. Both types of plasmids were digested with Hha I, which has no sites on the globin fragment but cleaves the viral DNA at 0.72 map units and the pBR322 DNA at a site 42 bp from the BamHI site. This generated SV40-globin recombinant molecules containing a 42 bp pBR322 "linker." These recombinant molecules were cyclized by treatment with DNA ligase, then used to infect African green monkey kidney cells together with tsA$_{239}$ SV40 DNA as the temperature-sensitive conditional lethal helper. Both resulting virus stocks contained approximately 50% helper and 50% recombinant virus. The recombinant viruses were shown to have the expected structurese by digestion with BamHI, Pst I, Hind III, Hinc II and various combinations of these enzymes.

EXAMPLE 2—Construction of SV40 (OY) recombinants carrying the mouse globin gene in two orientations The construction of the two SV40-globin hybrid viruses, SV$\alpha$1 and SV$\alpha$2, involved four steps shown in the figure: cloning of the mouse $\alpha$-globin and SV40 vector fragments in bacterial plasmids; recombination of these plasmids to generate "double recombinant" plasmids containing the $\alpha$-globin and SV40 fragments in both possible orientations relative to one another; cleavage of the "double recombinant" plasmids to yield pure SV40 globin recombinant molecules; and propagation of these molecules as virus particles by transfection of monkey kidney cells.

The source of the $\alpha$-globin gene was a 9700 base-pair fragment of chromosomal mouse DNA that was originally cloned in bacteriophage [Leder et al., Proc. Nat. Acad. Sci, 75, 1687–1691 (1978)].

This fragment was digested with Hinc II plus Sst I to generate a 2100 base-pair subfragment containig the complete $\alpha$-globin gene together with 1000 base pairs of 5' flanking and 250 base pairs of 3' flanking sequences. To facilitate cloning in SV40 and to assure that the mouse DNA could be inserted in both possible orientations, this subfragment was ligated to synthetic Eco RI octanucleotide linkers [Haynecker et al., Nature, 263, 748–752 (1976) and Scheller et al., Science, 196, 177–180 (1977)] and then cloned in the bacterial plasmid pBR322 [Bolivar et al., Gene 2, 95–113 (1977)] at its EcoRI site.

In a parallel experiment, wild-type SV40 DNA was cleaved with Hpa II at map position 0.72 and with Bam HI at map position 0.14 to generate the 3000 base pair vector fragment. This fragment was modified by ligation to Eco RI likers then cloned in pBR322.

"Double recombinant" plasmids containing both the mouse $\alpha$-globin gene and the SV40 vector fragment were constructed as follows. The pBR322-globin plasmid, whch has two Eco RI sites, was partially digested with Eco RI and full-length linear molecules were purified by gel electrophoresis. This DNA was ligated to the purified, Eco RI-linkered SV40 vector fragment, and the reaction mixture was introduced into E. coli by transformation. Plasmids carrying both $\alpha$-globin and SV40 sequences were identified by colony hybridization (Grunstein and Hogness, Proc. Nat. Acad. Sci. 72, 3961–3965, 1975), grown up, and examined by cleavage with several restriction endonucleases. As anticipated, four types of "double recombinants" were recovered, varying both in the orientation and site of insertion of the SV40 fragment. Two of the plasmids contained the $\alpha$-globin-coding sequences on the viral late strand (the source of SV$\alpha$1), whereas the other two contained the $\alpha$-globin-coding sequences on the viral early strand (the source of SV$\alpha$2).

Pure SV40-globin recombinant molecules were obtained by partial Eco RI digestion of the "double recombinant" plasmids followed by preparative agarose gel electrophoresis. These recombinant molecules (5100 base pairs) had approximately the same length as wild-type SV40 DNA (5200 base pairs) and therefore could be packages into virus particles. To accomplish this, monkey kidney cells were transfected with a mixture of the recombinant molecules plus DNA from a temperature-sensitive SV40 early gene mutant (SV40tsA239) as helper. The mixed infections were performed at 41° C., the non-permissive temperature for the helper virus. Under these conditions, progeny virus is formed only in those cells infected with both the recombinant molecule, which makes functional early gene products, and the helper, which makes all the necessary late gener products (Goff and Berg, Cell, 9, 695–705, 1976).

The resulting virus stocks were used to infect fresh cultures of monkey cells, and intracellular viral DNA was extracted and examined by restriction endonuclease cleavage and gel electrophoresis. The amounts of recombinant and helper genomes in these preparations were estimated by photographing the ethidium bromide-stained gels and scanning the negatives in a densitometer. This entire experiment was performed twice, using virus stocks derived from independent pBR322-globin-SV40 plasmid isolates for each experiment. In both experiments, the SV$\alpha$1 recombinants were efficiently replicated and encapsidated, leading to stocks containing about 50% recombinant genomes. In contrast, the SV$\alpha$2 stocks contained only 8–18% recombinant virus.

The structure of these recombinant viruses was confirmed by visualization of the R-loops formed with authentic globin mRNA. The viral DNAs were linearized with Bgl I, which cuts the SV40 genome at the origin of DNA replication, annealed with mRNA and examined in the electron microscope. As expected, both viruses showed three DNA-RNA hybrid loops, corresponding to the three α-globin-coding segments, separated by two short intervening sequences of double-stranded DNA. Because the first coding segment is substantially shorter than the second two, it is possible to determine the 5' to 3' orientation of the α-globin gene relative to the unique Bgl I restriction site in the SV40 vector DNA. In both cases, the appropriate orientation was observed in all of 50 molecules scored. These results confirm that the α-globin and SV40 late promoters are in tandem in SVα1 and opposed in SVα2, and also that the mouse gene has suffered no gross sequence rearrangements. The structures of the two recombinant viruses was also evaluated by cleavage with Eco RI, Pst I, Hinc II, and Bam HI plus Bgl I. In each case the expected set of fragments were observed.

The α-Globin mRNA is Translated

It has been shown that monkey cells infected with the two SV40-globin recombinant viruses produce α-globin mRNA that is structurally identical to its authentic counterpart. Monkey cells were infected with either SVα1 or SVα2, or with no virus or wild-type SV40 as controls, incubated until late in the lytic cycle, then labelled for 1 hr with $^3$H-leucine. Total cell proteins were extracted, immunoprecipitated with anti-mouse α-globin antibody, and separated according to molecular weight on a polyacrylamide-SDS gel. The resulting autoradiogram shows that cells infected with either SVα1 or SVα2 synthesize a protein that comigrates with authentic mouse α-globin and that is not found in mock or wild-type SV40 infected cells. (The additional bands seen in the control lanes are an artefact of the immunoprecipitation procedure.) This observation confirms the earlier conclusion that mouse globin gene translational signals are recognized in monkey cells (Hamer and Leder, 1979) and provides further evidence for the correct structure of the α-globin mRNA encoded by the recombinant viruses.

DNA transfections were carried out by inoculating approximately $2 \times 10^7$ confluent African green monkey kidney cells with 0.5 μg or 2.5 μg of recombinant DNA plus 0.2 μg of SV40 tsA239 helper DNA. The cells were fed with 100 ml medium, incubated at 40° C. for 10 days, then freeze-thawed. In all subsequent experiments, monolayers of about $2 \times 10^7$ monkey cells were infected with 2.5 ml of these lysates and incubated at 40° C. for 60 hr.

The structures of all plasmids, restriction fragments, and viruses used in this work were confirmed by cleavage with at least three restriction endonucleases. The hybrid genomes reach levels of about 100,000 copies per cell. Thus the monkey cells, which do not normally synthesize globin mRNA, are presented with the foreign globin gene as part of an active chromosome at high copy number. Under these conditions, the monkey cells produce substantial quantities of mouse α-globin mRNA that is structurally indistinguishable from its authentic counterpart.

EXAMPLE 3—Production of human growth hormone (hGH) using 28C

SV40-hGH Recombinants. The hGH1 and hGH2 genes were originally cloned in phage λ as 2.7 kb (kilobasepair) Eco RI fragments of human placental DNA (Tiddes et al., Proc. Nat. Acad. Sci., 76, 4294–4298, 1979). The two genes are approximately 95% homologous but can be distinguished from one another by the fact that gene 1 contains one BamHI site whereas gene 2 contains two sites. DNA sequencing shows that both the gene 1 and gene 2 Eco RI fragments contain approximately 500 base pairs of 5' flanking sequences and 550 base pairs of 3' flanking sequences as well as 5 hGH structural sequences (exons) separated by 4 intervening sequences (introns). The coding sequences of hGH1 are identical to those in cloned hGH complementary DNA suggesting that this gene is expressed into the major form of pituitary hGH. In contrast, the hGH2 gene differs from the cDNA by several base changes, fourteen of which are expected to lead to amino acid substitutions in the mature hormone.

The two different 2.7 kb hGH gene fragments were inserted, in both possible orientations, into an SV40 vector that retains the origin of viral DNA replication, a functional early gene region and the extreme 5' and 3' termini of the late gene region. In the SVhGH(L) recombinants the hGH1 and hGH2 genes are in the same orientation as SV40 late gene transcription whereas in the SVhGH(E) recombinants they are in the opposite or early orientation. These recombinant molecules were constructed by cloning into vector 28C in E. coli then propagated in monkey kidney cells as virions by mixed transfection with a temperature-sensitive early gene mutant of SV40 (SV40 tsA$_{239}$) as helper (Chow et al., J. Virol. 13, 1101–1109, 1974). The resulting stocks of virus contained approximately 10% SV40-hGH recombinant genomes and 90% helper genomes. These viral stocks were used to infect fresh monolayers of monkey kidney cells for all subsequent studies.

The ability of these recombinants to direct the synthesis of hGH was tested by labelling infected cells with $^3$H-leucine and analyzing the cellular proteins by immunoprecipitation and acrylamide-SDS gel electrophoresis. Cells infected with each of the four recombinants synthesized a protein that comigrated with authentic pituitary hGH and was absent from uninfected and wild type-SV40 infected controls. Both proteins are secreted into the media where they can be collected in highly enriched form.

Another example of protein expression by an SV40 vector, designated Y182 with hepatitis virus B antigen, is given in copending application, Ser. No. 304,571, filed concurrently now U.S. Pat. No. 4,442,205.

We claim:
1. A process for producing foreign proteins in eukaryotic cells comprising
   (a) cleaving SV40 at 0.14 map unit with BAM HI and 0.00 map unit with EcoRI to produce a SV-40 DNA fragment containing the origin of replication;
   (b) inserting said fragment into bacterial plasmid pBR322 together with pBR322 linkers between a single BAM HI site and a single EcoR1 site to produce pBR322-SV40;
   (c) after cloning cleaving pBR322-SV40 at the single BAM HI site and inserting a DNA fragment from a foreign gene therein;

(d) cloning the resulting recombinant plasmid in *E. coli;*

(e) remiving the plasmid pBR322 sequences by digesting the product with Hha I to generate SV-40 - foreign gene recombinant molecule containing a pBR322 linker;

(f) treating said recombinant molecule with appropriate DNA ligase to cyclize the recombinant molecule, then using said recombinant molecule to infect African green monkey kidney cells together with a temperature sensitive tsA$_{239}$ SV40 DNA as the temperature-sensitive conditional lethal helper.

2. The process in claim 1 in which the foreign gene fragment is one from the group consisting of: Mouse B$^{MAJ}$ globing and human growth hormone.

* * * * *

UNITED STATES PATENT OFFICE
CERTIFICATE OF CORRECTION

Patent No. 4,599,308         Dated   July 8, 1986

Inventor(s) Dean H. Hamer, Marian Kaehler, and Philip Leder

It is certified that error appears in the above-identified patent and that said Letters Patent are hereby corrected as shown below:

Column 6 Line 64

"EcoRl" should be corrected to read --EcoRI--

Column 7 Line 3

"remiving" should be corrected to read --removing--

Signed and Sealed this

Sixth Day of October, 1987

Attest:

DONALD J. QUIGG

Attesting Officer          Commissioner of Patents and Trademarks